US00PP08089P

United States Patent [19]

Craig

[11] Patent Number: Plant 8,089

[45] Date of Patent: Jan. 5, 1993

[54] GERANIUM PLANT 'JUBILEE'

[75] Inventor: Richard Craig, State College, Pa.

[73] Assignee: Research Corporation Technologies, Inc., Tuscon, Ariz.

[21] Appl. No.: 683,213

[22] Filed: Apr. 10, 1991

[51] Int. Cl.[5] ..... A01H 5/00

[52] U.S. Cl. ..... Plt./87.12

[58] Field of Search ..... Plt./68, 87.12

*Primary Examiner*—Howard J. Locker

*Attorney, Agent, or Firm*—Scully, Scott, Murphy & Presser

[57] ABSTRACT

This invention relates to a new and distinct cultivar of Geranium *Pelargonium*×*hortorum* named Jubilee that possesses a flower color that is a unique combination of red-orange and watermelon shades, and is early flowering, floriferous, self-branching, and compact.

1 Drawing Sheet

This invention was made with Government support under Hatch Act Funds awarded by the U.S. Department of Agriculture. The Government has certain rights in the invention.

SUMMARY OF THE INVENTION

The present invention relates to a new and distinct cultivar of Geranium *Pelargonium*×*hortorum* called 'Jubilee'. The cultivar is particularly well adapted to both commercial greenhouse production and garden performance. The cultivar is characterized by a semi-double flower whose flower color is a unique combination of red-orange and watermelon shades. The cultivar is early flowering, floriferous, self-branching and compact.

The cultivar was developed from an organized, scientifically designed breeding program conducted at the Department of Horticulture, The Pennsylvania State University, University Park, Pa. 16802. The breeding program combined European cultivars with exceptional flowering ability and compactness to create new cultivars with clear, bright flower colors.

Specifically, the cultivar resulted from selection in the progeny of the cross pollination between European geranium cultivars 'Jean Billes' and 'Honseler's Glorie Lila', reported to be a selection of 'Purpurball'. 'Jean Billes' has a clear salmon flower color and is vigorous. 'Honseler's Glorie Lila' is compact and magenta in flower color. 'Jubilee' possesses a combination of these colors. The selection was asexually propagated by cuttings in Pennsylvania and the reproductions ran true.

With reference to the detailed description of the cultivar which follows, the test plant was grown in a greenhouse under full natural light, at a night temperature of approximately 58° F., and a day temperature of approximately 68° F. Soilless medium was fertilized with every watering with 200 ppm nitrogen as 15-16-17. Color readings were taken under incandescent light at 200 foot candles and color identification was by reference to The Royal Horticultural Society Colour Charts, except where common terms of color definition are employed.

BRIEF DESCRIPTION OF THE DRAWINGS

The accompanying drawing is a color photograph illustrating the new cultivar, including foliage and flowers. The color in the photograph is as nearly true as is reasonably possible to make in a color illustration of this character.

DETAILED DESCRIPTION OF THE NEW VARIETY

THE PLANT

Classification:

*Botanical.*—*Pelargonium*×*hortorum.*

*Tradename*—#175-(83-16-3)='Jubilee'.

Form: Compact, self-branching.

Height: 230 to 280 mm.

Growth: Free branching from base; short internodes; excellent vigor.

Leaves:

*Size.*—Largest measured 70 mm long×115 mm wide; most length to width ratios were 2:3, some were 1:2.

*Shape.*—Reniform; variously lobed.

*Margin.*—Crenate.

*Texture.*—Pubescent.

*Color.*—Adaxial: Distal: Green 137A or 137B. Zone: Green 139A or yellow-green 147A, often faint. Proximal: Green 137A or 137B. Abaxial: Green 147B.

*Ribs and veins.*—Palmate venation; veins prominent.

Petioles:

*Length.*—85 to 140 mm.

*Color.*—Green 144A.

Stem:

*Internose length.*—13 to 20 mm.

*Color.*—Green 144A.

THE FLOWER

Blooming habit: Continuous.

Inflorescence

*Form.*—Umbellate.

*Size.*—Depends on number of florets; 80 to 110 mm, most about 100 mm.

Persistence: Persistent, non-shattering.

Disease resistance: Not known; favorable in outdoor trials.

Lasting quality: Excellent, usually 3 weeks or longer.

Florets:

*Number.*—32 to 47 (including unopened buds), most over 40.

*Forms.*—Cupped.

*Size.*—40 to 45 mm across when fully open.

*Petals.*—Number: 5 to 8, usually 5 to 6 larger petals with 1 to 3 smaller petals inside. Texture and Appearance: Smooth. Color: Adaxial: Distal one-third: A red 52A margin blending into 44B. Central one-third: Red 44B. Proximal one-third: Red 44B, some have a central spot that is red 52B. Abaxial: Distal margin: Red 39A or 39B. Center: Red 39A or 39B. Base: White 155D.

*Petaloids.*—Number: None observed.

*Sepals.*—Number: 5 to 6, most have 5.

*Pedicel.*—Length: 20 to 31 mm. Color: Green 144B.

Peduncle: Arises from node; opposed to leaf petiole; light pubescence.

*Length.*—120 to 172 mm; 4 mm wide.

*Color.*—Green 144A.

REPRODUCTIVE ORGANS

Androecium:

*Stamens.*—Up to 7 flat, ribbon-like filaments with purple tips, joined at their bases; versatile attachment to anthers which are purple; one pollen size; pollen is orange in color; 1 to 4 sterile stamens per floret.

*Staminodes.*—None observed.

*Petaloid stamens.*—2 to 4 petal-like filaments with partially developed anthers.

Gynoecium:

*Pistil.*—Number: 1. Length: 5.5 to 10.5 mm. Stigma: 1.5 to 2.5 mm. Style: 1 to 2 mm. Ovary: 3 to 4.5 mm; 5-parted; superior; very pubescent.

*Fruit.*—Schizocarp; opens into achene-like mericarp; rarely observed.

What is claimed is:

1. A new and distinct cultivar of Geranium substantially as illustrated and described herein, characterized as possessing a flower color that is a unique combination of red-orange and watermelon shades, and as being early flowering, floriferous, self-branching, and compact.

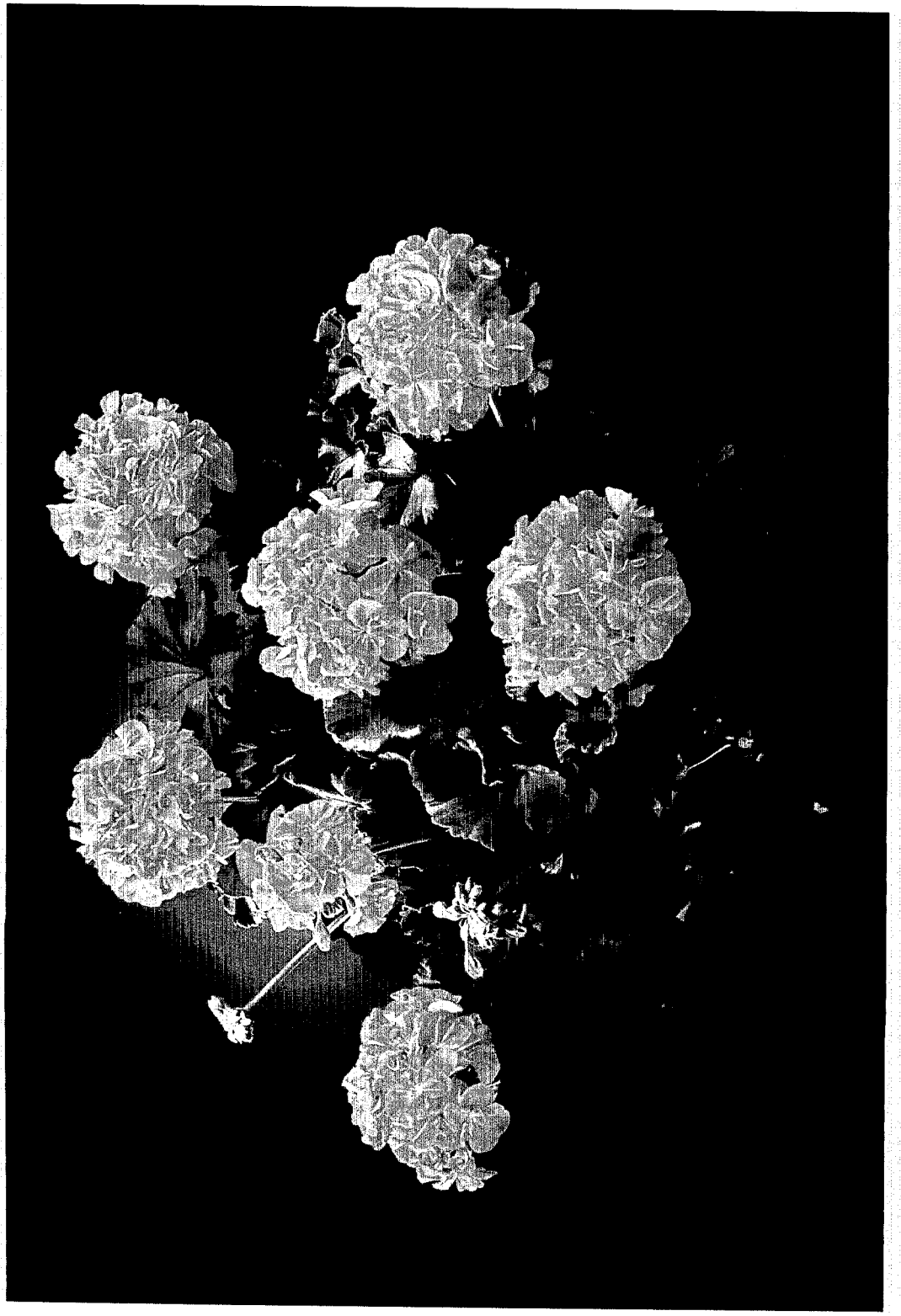

* * * * *